United States Patent
Feng et al.

(10) Patent No.: US 11,185,295 B2
(45) Date of Patent: Nov. 30, 2021

(54) IMAGING SYSTEMS AND METHODS THEREOF

(71) Applicant: UIH AMERICA, INC., Houston, TX (US)

(72) Inventors: Tao Feng, Houston, TX (US); Hongdi Li, Houston, TX (US)

(73) Assignee: UIH AMERICA, INC., Houston, TX (US)

(*) Notice: Subject to any disclaimer, the term of this patent is extended or adjusted under 35 U.S.C. 154(b) by 0 days.

(21) Appl. No.: 16/845,909

(22) Filed: Apr. 10, 2020

(65) Prior Publication Data

US 2020/0237321 A1 Jul. 30, 2020

Related U.S. Application Data

(63) Continuation of application No. 15/602,285, filed on May 23, 2017, now Pat. No. 10,617,366.

(51) Int. Cl.
| | | |
|---|---|---|
| *A61B 6/03* | (2006.01) | |
| *A61B 6/00* | (2006.01) | |
| A61B 6/04 | (2006.01) | |

(52) U.S. Cl.
CPC ............ *A61B 6/037* (2013.01); *A61B 6/4291* (2013.01); *A61B 6/503* (2013.01); *A61B 6/0407* (2013.01)

(58) Field of Classification Search
CPC ....... A61B 6/037; A61B 6/4291; A61B 6/503; A61B 6/0407
See application file for complete search history.

(56) References Cited

U.S. PATENT DOCUMENTS

| | | | |
|---|---|---|---|
| 2008/0135768 A1* | 6/2008 | Chang | A61B 6/037 250/363.04 |
| 2008/0137806 A1 | 6/2008 | Chang | |
| 2010/0001190 A1 | 1/2010 | Wieczorek et al. | |
| 2012/0108948 A1* | 5/2012 | Jansen | A61B 6/4258 600/411 |
| 2012/0248320 A1* | 10/2012 | Wangerin | A61B 6/037 250/363.05 |

(Continued)

FOREIGN PATENT DOCUMENTS

CN 1856272 A 11/2006

OTHER PUBLICATIONS

Kjell Erlandsson et al., Performance Evaluation of D-SPECT: A Novel SPECT System for Nuclear Cardiology, Physics in Medicine & Biology, 54(9): 2635-2649, 2009.

(Continued)

*Primary Examiner* — Hugh Maupin
(74) *Attorney, Agent, or Firm* — Metis IP LLC

(57) ABSTRACT

An imaging system includes a collimator assembly, a detector assembly and a control device. The collimator assembly is configured to collimate photons emitted from an imaged subject. The collimator assembly includes a plurality of slit-plates, each of the plurality slit-plates including one or more slits configured to collimate the photons in a first direction, and a plurality of slats parallel to a transverse plane of the imaging system. The detector assembly is configured to generate signals based on the collimated photons. The control device is configured to place the plurality of slit-plates in a plurality of locations to provide a plurality of fields of view of the imaging system.

20 Claims, 9 Drawing Sheets

(56) References Cited

U.S. PATENT DOCUMENTS

2014/0077095 A1     3/2014   Deprez et al.
2014/0319360 A1    10/2014   Wieczorek et al.

OTHER PUBLICATIONS

Laetitia Imbert et al., Compared Performance of High-Sensitivity Cameras Dedicated to Myocardial Perfusion SPECT: A Comprehensive Analysis of Phantom and Human Images, Journal of Nuclear Medicine, 53(12): 1897-1903, 2012.
Wei Chang et al., C-SPECT—Clinical Cardiac SPECT/Tct Platform: Design Concepts and Performance Potential, IEEE Transactions on Nuclear Science, 56(5): 2659-2671, 2009.
First Office Action in Chinese Application No. 201810500192.0 dated Apr. 1, 2021, 21 pages.

\* cited by examiner

IMAGING SYSTEMS AND METHODS THEREOF

CROSS-REFERENCE TO RELATED APPLICATIONS

This application is a continuation of U.S. application Ser. No. 15/602,285, filed on May 23, 2017, the contents of which are hereby incorporated by reference.

TECHNICAL FIELD

The present disclosure generally relates to imaging systems, and more particularly to collimation mechanisms for imaging systems such as a single photon emission tomography (SPECT) system.

BACKGROUND

Nuclear medicine tomographic imaging techniques, such as single photon emission tomography (SPECT), use electromagnetic radiation to produce images of a patient. For example, the SPECT technique requires administration of a radionuclide to the patient. Gamma photons are emitted by the radionuclide as the radionuclide decays. The emitted gamma photons are detected to produce signals related to the patient (e.g., cross-sectional images). Multiple images can be acquired from multiple angles to construct 3-D image data.

SUMMARY

In an aspect of the present disclosure, an imaging system is provided. The system may include a collimator assembly, a detector assembly and a control device. The collimator assembly may be configured to collimate photons emitted from an imaged subject. The collimator assembly may further include a plurality of slit-plates, each of the plurality slit-plates including one or more slits configured to collimate the photons in a first direction, and a plurality of slats parallel to a transverse plane of the imaging system. The detector assembly may be configured to generate signals based on the collimated photons. The control device may be configured to place the plurality of slit-plates in a plurality of locations to provide a plurality of fields of view of the imaging system.

In some embodiments, the plurality of slit-plates and the plurality of slats may be physically separated.

In some embodiments, the slit-plates may be curved plates including multiple axially oriented slits, and the one or more slits may be perpendicular to the transverse plane of the imaging system.

In some embodiments, the plurality of slats may be placed between the slit-plates and the detector assembly for collimating the photons in a second direction.

In some embodiments, the slats may be extended radially on a surface of the detector assembly.

In some embodiments, the plurality of fields of view may comprise a first field of view corresponding to a first scanning mode for scanning a first body part and a second field of view corresponding to a second scanning mode for scanning a second body part.

In some embodiments, the control device may be configured to move at least one of the slit-plates from a first location to a second location to switch between the first scanning mode and the second scanning mode.

In some embodiments, the control device may include an annular plate connected to the at least one of the slit-plates.

In some embodiments, to control at least one of the slit-plates to be moved from a first location to a second location, the control device may be configured to control the annular plate to rotate around an axis of the annual plate from a first angle to a second angle.

In some embodiments, the plurality of slit-plates may include a first number of slit-plates in a first segment in the axial direction and a second number of slit-plates in a second segment in the axial direction, and wherein the first number is different from the second number.

In some embodiments, the axial direction may be perpendicular to the transverse plane of the imaging system.

In some embodiments, the control device may include an actuating device, the control device configured to place the one or more slit-plates in the plurality of locations to provide the plurality of fields of view of the imaging system using the actuating device. In some embodiments, the plurality of slit-plates may form a bore configured to accommodate the imaged subject, and the system may further include a bore adjusting device configured to adjust the diameter of the bore.

In another aspect of the present disclosure, an imaging system is provided. The system may include a collimator assembly, a detector assembly and one or more control devices. The collimator assembly may include a plurality of slit-plates, each of the plurality slit-plates including one or more slits; and a plurality of slats defining a number of channels between each two of the adjacent slats, the channels arranged nonparallel to the one or more slits. The detector assembly may be placed outside of the collimator assembly. The one or more control devices may be configured to adjust relative positions between the slit-plates and the detector assembly to obtain an adjustable field of view (FOV) surrounded by the slit-plates.

In some embodiments, the channels may be substantially perpendicular to the slits.

In some embodiments, the slats may be arranged in fixed manner regarding to the detector assembly, and the slats may be configured to be placed at a plurality of location relative to the detector assembly.

In some embodiments, the one or more control devices may include two control devices located at opposite ends of the detector assembly.

In a further aspect of the present disclosure, a method of adjusting collimator assembly performance may be provided. The method may include moving axially at least one of a plurality of slit-plates of a collimator assembly or one of a plurality of slats of the collimator assembly to concurrently adjust a size of a field of view (FOV) surrounded by the collimator assembly; wherein a detector assembly may be placed outside of the collimator assembly, wherein each of the plurality of slit-plates may include one or more slits; wherein the plurality of slats may define a number of channels between each two of the adjacent slats; and wherein the channels may be arranged non-parallel to the one or more slits.

In some embodiments, moving axially at least one of the plurality of slit-plates of the collimator assembly or one of the plurality of slats of the collimator assembly may include rotating at least one of a plurality of slit-plates or one of a plurality of slats.

In some embodiments, the method may further include forming the collimator assembly with at least one opening from the plurality of slit-plates arranged in a ring configuration to form the opening.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
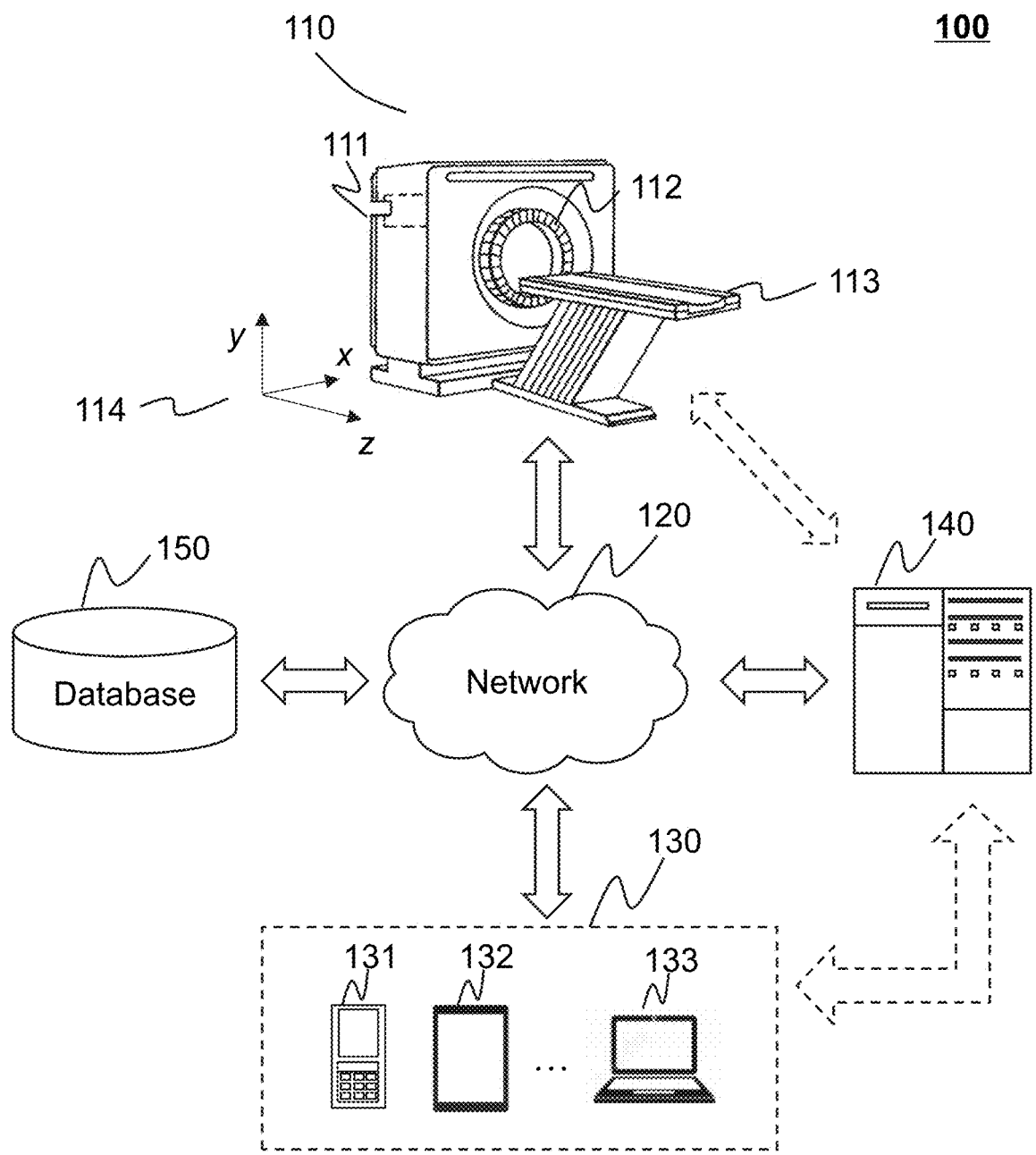
FIG. 1 is a schematic diagram illustrating an exemplary imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 250 as illustrated in FIG. 2B) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging, such as for disease diagnosis or research purposes. In some embodiments, the imaging system may be a single photon emission computed tomography (SPECT) system. In some embodiments, the imaging system may be a multi-modality system, which combines a SPECT system with other types of imaging systems including, for example, an emission computed tomography (ECT) system, a positron emission tomography (PET) system, or the like, or any combination thereof.

An imaging system, such as a SPECT system, may include a collimator assembly that can filter a stream of photons to allow photons travelling in a particular direction to pass through. Imaging of different parts of a patient (e.g., the head, the body, the heart) may require different collimator assemblies to achieve various fields of view (FOVs), sensitivity, and/or resolutions.

Conventional SPECT systems need a user to change another collimator assembly manually when its FOV is changed. This may increase the user's radiation exposure, as well as reduce efficiency in clinical diagnosis. In addition, conventional SPECT techniques used detector rings of circular cross sections to perform whole body imaging. The shape of the cross-section of a conventional detector ring is different from that of a cross section of a patient. As such, the FOV of the conventional detector ring is not fully utilized in whole body imaging. Furthermore, conventional SPECT techniques used an FOV including only the heart for cardiac imaging, which may cause interior problems and reduce image quality.

Aspects of the present disclosure address the above-mentioned deficiencies by providing an imaging system that can automatically provide desirable resolutions, sensitivity, and/or FOVs for various scanning modes. The scanning modes may correspond to imaging of various parts of a patient, such as the heart, the body, the head, etc. The imaging system may include a collimator assembly configured to collimate photons emitted from an imaged subject (e.g., a patient, a non-human object, etc.). The collimator assembly can include a plurality of slit-plates and slates. The slit-plates can form one or more slits to collimate the photons in a first direction. The slats may be configured to collimate the photons in a second direction. In some embodiments, the slats may be positioned parallel to a transverse plane of the imaging system. The imaging system can also include a detector assembly for detecting the photons. In some embodiments, a cross-section of the detector assembly can be oval or elliptical.

FIG. 1 is a schematic diagram illustrating an exemplary imaging system according to some embodiments of the present disclosure. In some embodiments, the imaging system 100 may be a SPECT system. As shown, the imaging system 100 may include a scanner 110, a network 120, one or more terminals 130, a computing device 140, and a database 150.

The scanner 110 may include a gantry 111, a detector assembly 112, a table 113, and a collimator assembly (not shown). The gantry 111 may support the detector assembly 112 and the collimator assembly. An imaged subject may be placed on the table 113 for SPECT scanning. Prior to the SPECT scanning, a radioisotope (e.g., a radiopharmaceutical substance) may be administered to the imaged subject. The radioisotope may emit photons (e.g., gamma photons) during its decay process. The collimator assembly may be located between the imaged subject and the detector assembly 112 for collimating the photons emitted from the imaged subject. The detector assembly 112 may detect the collimated photons and generate one or more signals based on the detected photons. The one or more signals may include image data of the imaged subject.

In some embodiments, the scanner 110 may be a single-modality scanner, for example, a photon emission computed tomography (SPECT) scanner. In some embodiments, the scanner 110 may be a multi-modality scanner, which combines a SPECT scanner with other types of scanners including, for example, an emission computed tomography (ECT) scanner or a positron emission tomography (PET) scanners.

In some embodiments, a reference coordinate system 114 may be established. The reference coordinate system 114 may relate to SPECT scanning, data acquisition, image reconstruction, etc. In some embodiments, the longitudinal direction of the table 113 may be defined as the z-direction. A plane that is perpendicular to the z-direction (e.g., a transverse plane of a body part of an imaged subject) may be defined as a x-y plane (also referred to as a transverse plane of the imaging system 100).

The network 120 may facilitate exchange of information and/or data for the imaging system 100. In some embodiments, one or more components of the imaging system 100 (e.g., the scanner 110, the terminal 130, the computing device 140, the database 150, etc.) may communicate information and/or data with one or more other components of the SPECT system 100 via the network 120. For example, the computing device 140 may obtain signals from the scanner 110 via the network 120. As another example, the computing device 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 may communicate with the scanner 110, and/or the computing device 140. For example, a user may set a scanning parameter for the scanner 110 via the terminal(s) 130. As another example, the terminal(s) 130 may acquire a SPECT image from the computing device 140. The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the computing device 140.

The computing device 140 may process data and/or information obtained from the scanner 110, the terminal 130, and/or the database 150. For example, the computing device 140 may process signals obtained from the scanner 110 and reconstruct a SPECT image. In some embodiments, the computing device 140 may be a computer, a user console, a single server or a server group, etc. The server group may be centralized or distributed. In some embodiments, the computing device 140 may be local or remote. For example, the computing device 140 may access information and/or data stored in the scanner 110, the terminal 130, and/or the database 150 via the network 120. As another example, the computing device 140 may be directly connected to the scanner 110, the terminal 130 and/or the database 150 to access stored information and/or data. In some embodiments, the computing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The database 150 may store data, instructions, and/or any other information. In some embodiments, the database 150 may store data obtained from the terminal 130 and/or the computing device 140. In some embodiments, the database 150 may store data and/or instructions that the computing device 140 may execute or use to perform exemplary methods described in the present disclosure. In some embodiments, the database 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the database 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the database 150 may be connected to the network 120 to communicate with one or more other components in the imaging system 100 (e.g., the computing device 140, the terminal 130, etc.). One or more components in the imaging system 100 may access the data or instructions stored in the database 150 via the network 120. In some embodiments, the database 150 may be directly connected to or communicate with one or more other components in the image system 100 (e.g., the computing device 140, the terminal 130, etc.). In some embodiments, the database 150 may be part of the computing device 140.

Figure 2A:
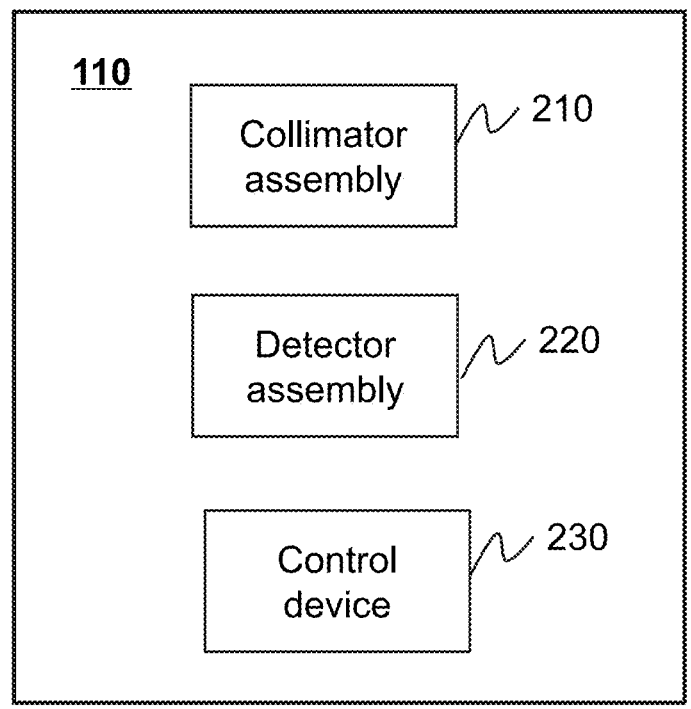
FIG. 2A is a schematic diagram illustrating an exemplary scanner according to some embodiments of the present disclosure.
Figure 2B:
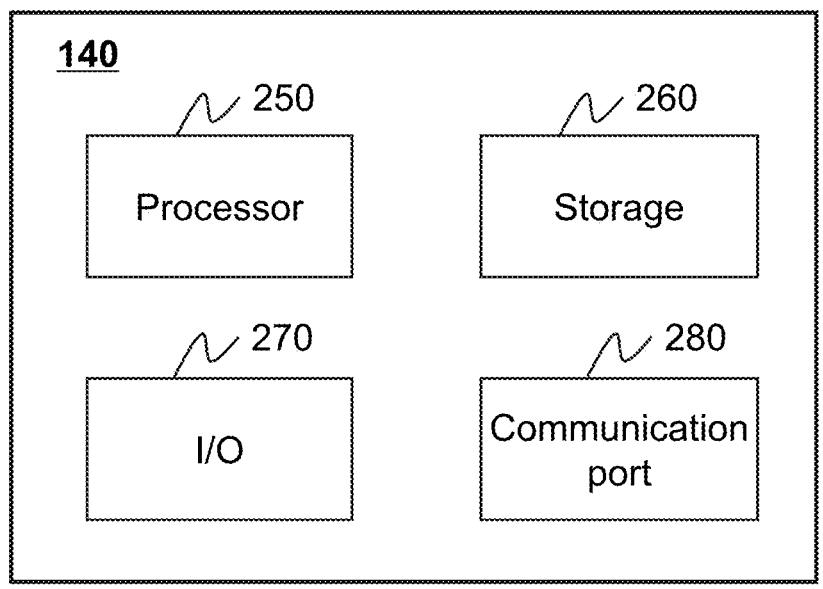
FIG. 2B is a schematic diagram illustrating an exemplary computing device according to some embodiments of the present disclosure.

FIG. 2A is a schematic diagram illustrating an exemplary scanner according to some embodiments of the present disclosure. As illustrated in FIG. 2A, the scanner 110 may include a collimator assembly 210, a detector assembly 220 and a control device 230.

The collimator assembly 210 may collimate photons emitted from an imaged subject. The collimator assembly 210 may be placed between an imaged subject and the detector assembly 220 for surrounding the imaged subject and collimating photons from the imaged subject. In some embodiments, the collimator assembly 210 may include a plurality of sections. The plurality of sections may be configured as a flexible shape, for example, a bore. The shape, size, and/or location of the flexible shape may be adjustable. In some embodiments, the plurality of the sections may be coupled to the control device 230, and the shape, size, and/or location of the flexible shape may be adjusted by the control device 230. In some embodiments, each of the plurality of sections may include a plurality of openings. Photons from a field of view may pass through the plurality of opening and reach the detector assembly 220. Merely for illustration purposes, the plurality of openings may be holes (e.g., parallel holes, divergent holes, convergent holes, a pinhole, etc.), gaps, etc. The collimator assembly 210 may collimate photons in certain directions using the plurality of opening.

In some embodiments, the collimator assembly 210 may include a plurality of slit-plates. The slit-plates may be movable relative to the detector assembly 220. In some embodiments, the slit-plates may be configured as a flexible shape. The slit-plates may further include one or more slits. In some embodiments, the slit-plates may be curved plates including multiple axially oriented slits. The slits may be grooves with certain lengths and widths. The slits may collimate photons in certain directions. In some embodiments, the collimator assembly 210 may further include a plurality of slats. The slats may be placed between the slit-plates and the detector assembly 220. In some embodiments, the slats may collimate photons in another direction (e.g., a direction perpendicular to the direction of the slit). In some embodiments, the slit-plates and the slats are physically separated.

The detector assembly 220 may detect photons from a FOV. The detector assembly 220 may be placed behind the collimator assembly 210 to detect collimated photons. The detector assembly 220 may generate one or more signals based on the detected photons. In some embodiments, the one or more signals may be transmitted to a computing device, for example, the computing device 140, to reconstruct an image.

In some embodiments, the detector assembly 220 may include one or more detector units. The detector units may include a scintillator, a light sensitive element (e.g., photomultiplier tube, photodiodes, optoelectric transducer, etc.), semiconductor crystals, or the like, or a combination thereof. In some embodiments, the detector assembly 220 may have a plurality of sizes or shapes. Merely by ways of example, the cross-section of the detector assembly 220 may be an arc, an oval, a circle, a polygon, etc. In some embodiments, the detector assembly 220 may be an oval-shaped detector. In some embodiments, the detector assembly 220 may be stationary relative to the reference coordinate system 114.

The control device 230 may perform particular functions relate to a scanning of a body part of an imaged subject. In some embodiments, the control device 230 may drive the table 113 to move in the z-direction. During the moving process, the detector assembly 220 may detect photons from a body part of the imaged subject and generate signals based on the detected photons.

In some embodiments, the control device 230 may place the slit-plates of the collimator assembly 210 in a plurality of locations. At different locations, the detector assembly 220 may detect photons from different FOVs. For example, the control device 230 may include a mechanical device. The mechanical device may connect to one or more slit-plates of the collimator assembly 210. The control device 230 may drive the one or more slit-plates to different locations by moving the mechanical device in certain directions (e.g., a direction in the z-direction) to achieve desirable resolutions, sensitivity, and/or FOVs.

It should be noted that the above description of the scanner 110 is merely provided for the purposes of illustration, and not intended to limit the scope of the present disclosure. For persons having ordinary skills in the art, multiple variations and modifications may be made under the teachings of the present disclosure. For example, the assembly and/or function of the scanner 110 may be varied or changed according to specific implementation scenarios. As another example, the scanner 110 may further include a patient positioning system for adjusting the position of an imaged subject relative to the table 113. However, those variations and modifications do not depart from the scope of the present disclosure.

FIG. 2B is a schematic diagram illustrating an exemplary computing device according to some embodiments of the present disclosure. As illustrated in FIG. 2B, the computing device 140 may include a processor 250, a storage 260, an input/output (I/O) 270, and a communication port 280.

The processor 250 may execute computer instructions (e.g., program code) and perform functions of the computing device 140 in accordance with techniques described herein. The computer instructions may include, for example, routines, programs, objects, components, data structures, procedures, modules, and functions, which perform particular functions described herein. For example, the processor 250 may perform image reconstruction operations to reconstruct a SPECT image based on lone or more signals. The one or more signals may be obtained from the scanner 110, the terminal 130, the database 150, and/or any other component of the imaging system 100. In some embodiments, the processor 250 may reconstruct the SPECT image based on one or more algorithms, such as filtered back projection, inverse matrix, etc.

In some embodiments, the processor 250 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 140. However, it should be noted that the computing device 140 in the present disclosure may also include multiple processors, thus operations and/or method steps that are performed by one processor as described in the present disclosure may also be jointly or separately performed by the multiple processors.

The storage 260 may store data/information obtained from the scanner 110, the terminal 130, the database 150, and/or any other component of the imaging system 100. In some embodiments, the storage 260 may include a mass storage, a removable storage, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 260 may store one or more programs and/or instructions to perform exemplary methods described in the present disclosure. For example, the storage 260 may store a program for the computing device 140 for reconstructing a SPECT image based on image obtained from the scanner 110.

The I/O 270 may input and/or output signals, data, information, etc. In some embodiments, the I/O 270 may enable a user interaction with the computing device 140. In some embodiments, the I/O 270 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 280 may be connected to a network (e.g., the network 120) to facilitate data communications. The communication port 280 may establish connections between the computing device 140 and the scanner 110, the terminal 130, and/or the database 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 280 may be and/or include a standardized communication port, such as RS232, RS485, etc. In some embodiments, the communication port 280 may be a specially designed communication port. For example, the communication port 280 may be designed in accordance with the digital imaging and communications in medicine (DICOM) protocol.

Figure 3:
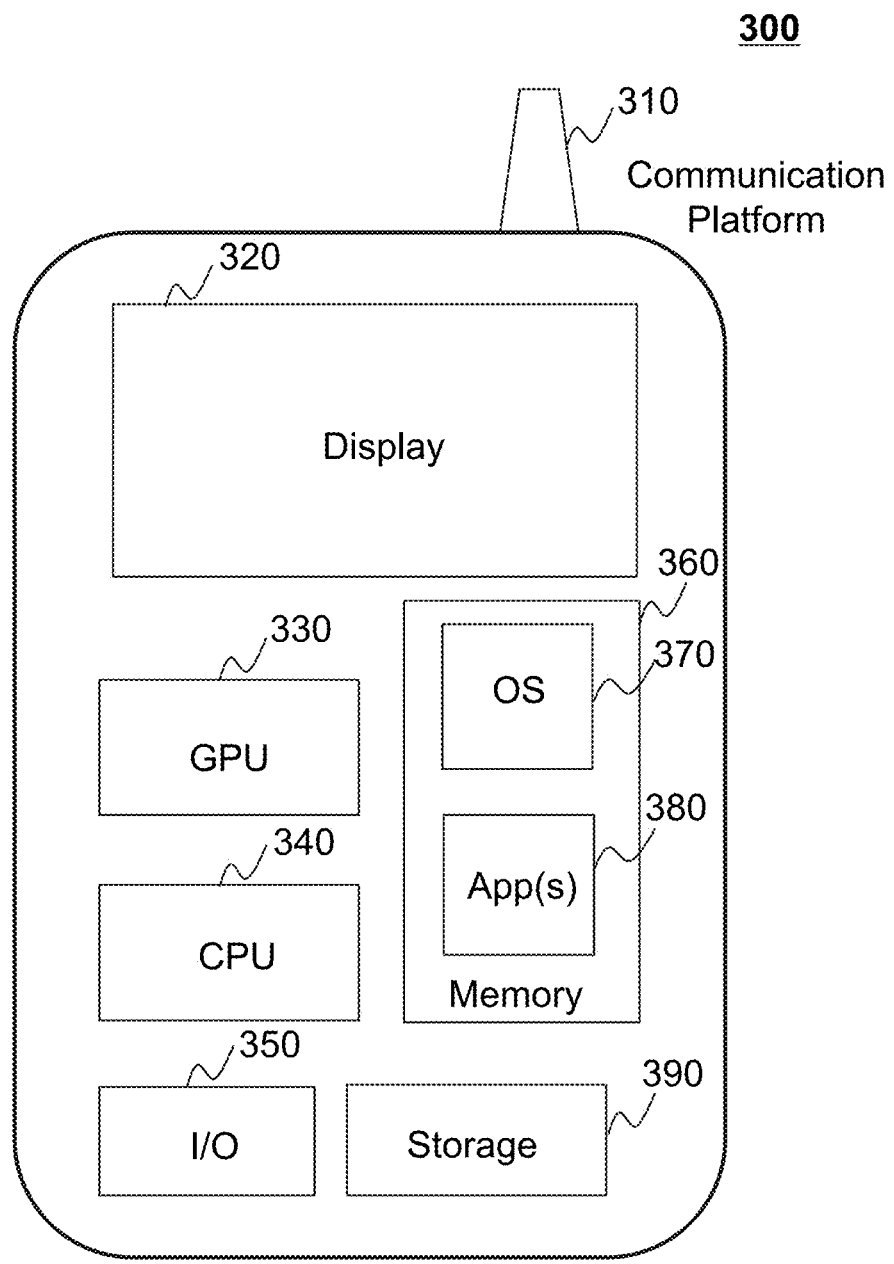
FIG. 3 is a schematic diagram illustrating exemplary hardware and/or software components of an exemplary mobile device 300 on which the terminal 130 may be implemented according to some embodiments of the present disclosure.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image reconstruction or other information from the computing device 140. User interactions with the information stream may be achieved via the I/O 350 and provided to the computing device 140 and/or other components of the imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4A:
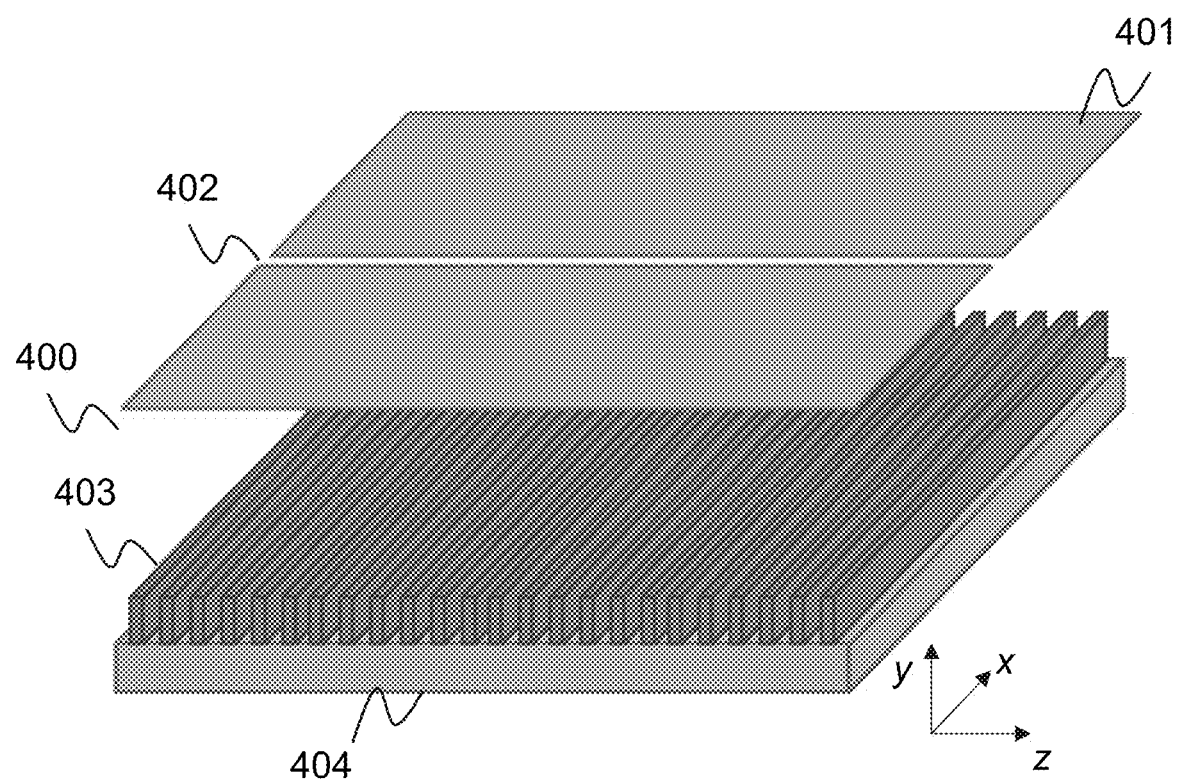
FIG. 4A is a schematic diagram illustrating an exemplary structure of a collimator assembly according to some embodiments of the present disclosure.

FIG. 4A is a schematic diagram illustrating an exemplary structure of a collimator according to some embodiments of the present disclosure. The structure 400 may be provided for illustration purposes, in some embodiments, the structure 400 may be a part of a collimator assembly, which may be configured as a flat plate or a curved plate. The structure 400 may include a slit-plate 401 and a plurality of slats 403.

The slit-plate 401 may include a slit 402. The slit 402 may be an opening through which photons may pass. As illustrated in FIG. 4A, the slit 402 may be aligned with the z-direction of the reference coordinate system 114 (i.e., the slit is perpendicular to the transvers plane of the imaging system 100). The slit 402 may collimate photons in the z-direction. The slit 402 may have a certain width. The width of the slit 402 may relate to spatial resolution and photon sensitivity of the imaging system 100. In some embodiments, the width of the slit 402 may be determined according to default settings or certain requirements of the imaging system 100. In some embodiments, the slit 402 may have other shapes. For example, the slit 402 may be a curve, a wavy line, a broken line, etc.

The plurality of slats 403 may be positioned between the slit-plate 401 and the detector assembly 404. In some embodiments, the plurality of slats 403 may be fixed or extended radially on a surface of the detector assembly 404. The plurality of slats 403 may be configured as evenly distributed strips that form a plurality of openings. Photons may pass through the openings and reach the detector assembly 404. The width of the opening may also relate to spatial resolution and photon sensitivity of the imaging system 100. In some embodiments, the width of the opening may be adjusted by increasing/decreasing the number of the slats 403 according to default settings or certain requirements of the imaging system 100. The direction of the plurality of slats 403 may be perpendicular to the slit 402. Thus the slats 403 may be positioned in the x-direction of the reference coordinate system 114 for collimating photons in the x-direction. In some embodiments, the plurality of slats 403 may be positioned in the y-direction, or any other direction along the x-y plane of the reference coordinate system 114 for collimating photons in the corresponding direction. The plurality of slats 403 may define a number of channels between each two of the adjacent slats, the channels arranged nonparallel to the slit 402.

In some embodiments, the slit-plate may include one or more parts. The one or more parts may refer to different segments of the slit-plate in the z-direction. In some embodiments, the number and/or the positions of the slits included in one or more parts of a slit-plate may be different. For example, a first part of the slit-plate corresponding to a range from z=0~10 in the reference coordinate system 114 may include twenty slits. A second part of the slit-plate from z=10~20 may include one hundred slits.

It should be noted that the above description of the structure 400 is merely provided for the purposes of illustration, and not intended to limit the scope of the present disclosure. For persons having ordinary skills in the art, multiple variations and modifications may be made under the teachings of the present disclosure. For example, the slit-plate 401 may not be parallel to the detector assembly 404 as illustrated in FIG. 4A. However, those variations and modifications do not depart from the scope of the present disclosure.

Figure 4B:
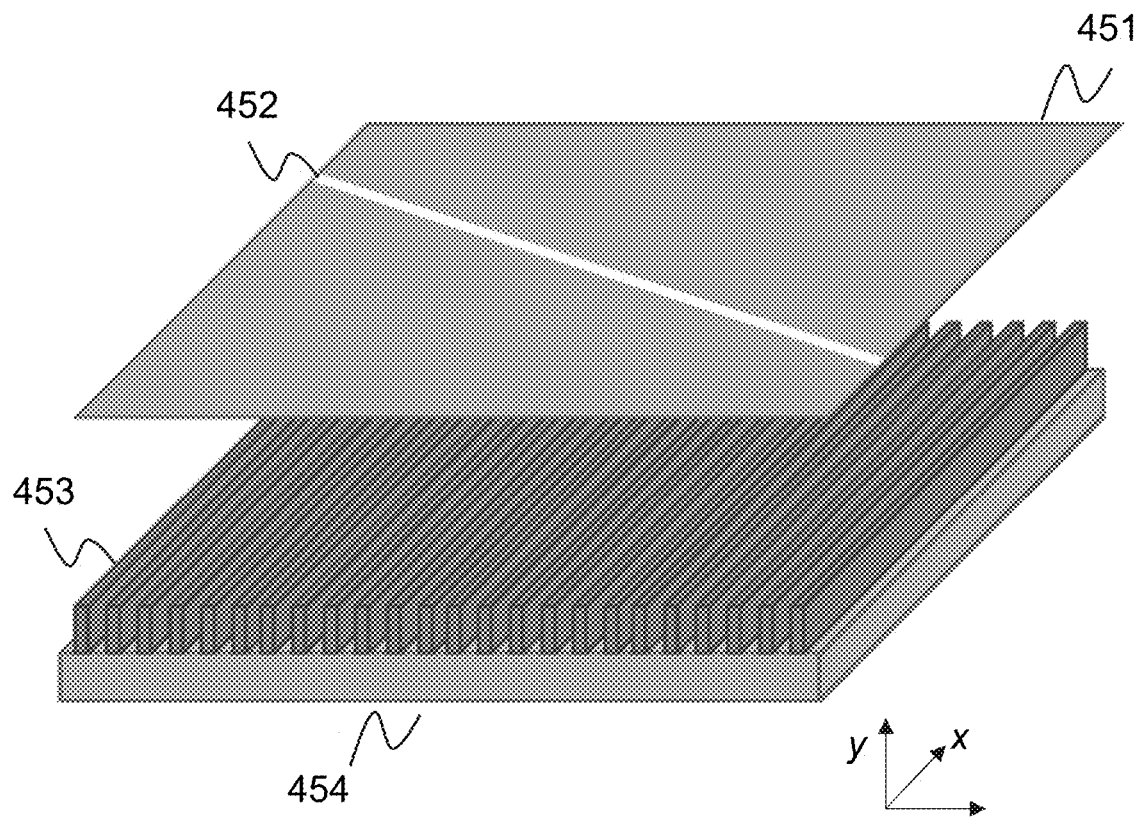
FIG. 4B is a schematic diagram illustrating an exemplary structure of a collimator assembly according to some embodiments of the present disclosure.

FIG. 4B is a schematic diagram illustrating an exemplary structure of a collimator assembly according to some embodiments of the present disclosure. The structure 450 may include a slit-plate 451, and a plurality of slats 453. The slit-plate 451 may also include a slit 452 thereon. In some embodiments, the slit-plate 451 may be parallel to the detector assembly 454. FIG. 4B illustrates a similar collimator assembly structure as described with reference to FIG. 4A except that the slit 452 on the slit-plate 451 may be set in a direction different from the direction in which slit 402 be set. In some embodiments, slit 452 may be in any-direction except the direction perpendicular to the z-direction.

FIGS. 5A through 5D are schematic diagrams illustrating exemplary cross sections of slit-plates in different scanning modes according to some embodiments of the present disclosure. The imaging system 100 may implement a plurality of scanning modes. In some embodiments, the plurality of scanning modes may be used for scanning different body parts of an imaged subject. For example, the scanning modes may include a first scanning mode, a second scanning mode, a third scanning mode, etc. The first scanning mode, the second scanning mode, and the third scanning mode may correspond to scanning of a first body part, a second body part, and a third body part, respectively. The first scanning mode, the second scanning mode, and the third scanning mode may correspond to a first FOV, a second FOV, and a third FOV, respectively. The first FOV, the second FOV, and the third FOV may or may not be the same. Merely for illustration purposes, a head scanning mode may be used for scanning the head of a patient; a whole-body scanning mode may be used for scanning the whole body of a patient; and a heart scanning mode may be used for scanning the heart of a patient. In some embodiments, each of the plurality of the scanning modes may have different scanning parameters, for example, FOV, spatial resolution, sensitivity, or the like, or a combination thereof. For example, a whole-body scanning mode may need a larger FOV than a head scanning mode and a heart scanning mode. As another example, the heart scanning mode may need a larger sensitivity than the whole-body scanning mode and the head scanning mode.

Figure 5A:
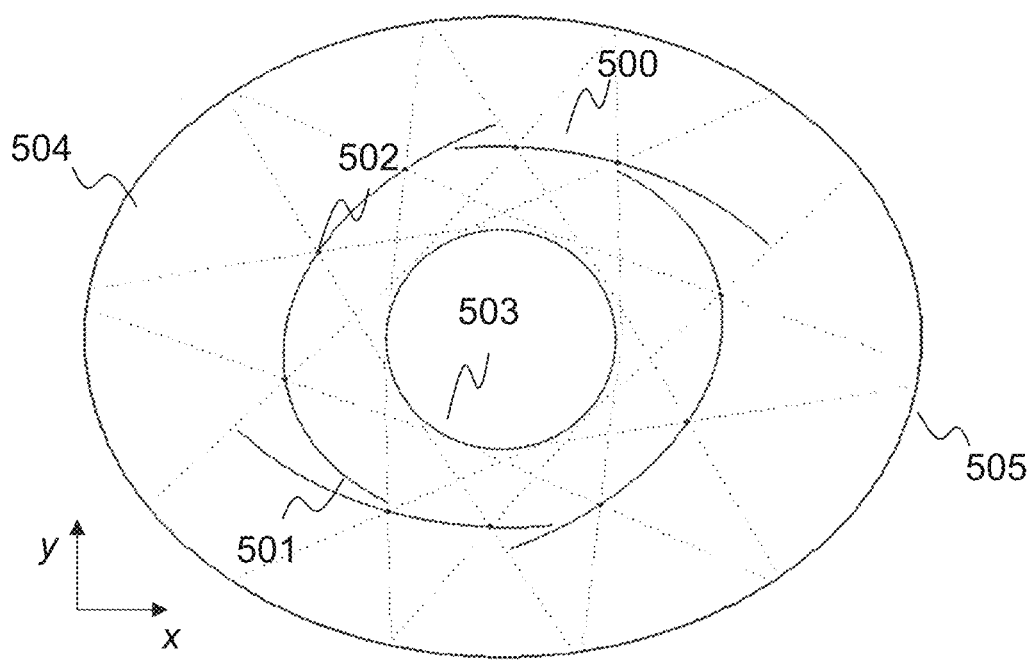
FIGS. 5A through 5D are schematic diagrams illustrating exemplary cross sections of slit-plates in different scanning modes according to some embodiments of the present disclosure.

Referring to FIG. 5A, a cross section of the slit-plates of a collimator assembly in the head scanning mode may be illustrated. The collimator assembly 500 may include a plurality of (e.g., four) slit-plates and a plurality of slats (not shown). Each of the plurality of slit-plates may include one or more slits. The detector assembly 505, behind the collimator assembly 500, may be stationary relative to the reference coordinate system 114. In some embodiments, the cross section of the detector assembly 505 may be oval. The detector assembly 505 may detect photons from a FOV 503, and generate signals based on the detected photons.

In some embodiments, in the head scanning mode, the FOV 503 may be circular. In some embodiments, the FOV 503 may be centered on the axis of the detector assembly 505. The FOV 503 may have a plurality of sizes. In some embodiments, the size of the FOV 503 may relate to the size of the head of patients. For example, the FOV 503 may be larger for adults, and may be smaller for kids. The shape, location, and/or size of the FOV 503 may be set by a user (e.g., a doctor), according to a default setting of the imaging system 100, etc. In some embodiments, the scanner 110 may further include a patient positioning device for placing an imaged body part to a predetermined location. For example, the patient positioning unit may place the head of a patient in the FOV 503.

The slit-plates may be positioned at certain locations during the head scanning mode. In some embodiments, the locations of the slit-plates may be predetermined by a user, or according to a default setting of the imaging system 100, or a combination of both. In some embodiments, the location of slit-plates may be determined according to one or more scanning parameters including, for example, FOV, spatial resolution, and/or sensitivity. In the head scanning mode, the locations of slit-plates may be determined according to the resolution and/or FOV the of the imaging system 100. The resolution may relate to the distance between the slits on the plurality of slit-plates and the detector assembly 505. For example, a longer distance between the slits and the detector assembly 505 may lead to a higher resolution.

In some embodiments, in the head scanning mode, the plurality of slit-plates may be positioned at certain locations to encompass the FOV 503. In some embodiments, the shape formed by the slit-plates may be circular. As illustrated in FIG. 5A, the four slit-plates may roughly form a circle encompassing the FOV 503.

In some embodiments, the number of slits used in the head scanning mode may depend on the FOV and the locations of the slit-plates. In the x-y plane, the slits may function as one-dimensional pinholes. Photons from the FOV 503 may pass through the slits, and form a plurality of projections on the detector assembly 505. The detector assembly 505 may generate signals based on the projections. Taking a slit 502 on a slit-plate 501 as an example, photons that pass through the slit 502 may form a projection 504 on detector assembly 505. In some embodiments, the slits may be set according to the projections on the detector assembly 505. For example, a proper number of slits be determined when the detector 505 assembly has accommodated a largest number of projections.

Figure 5B:
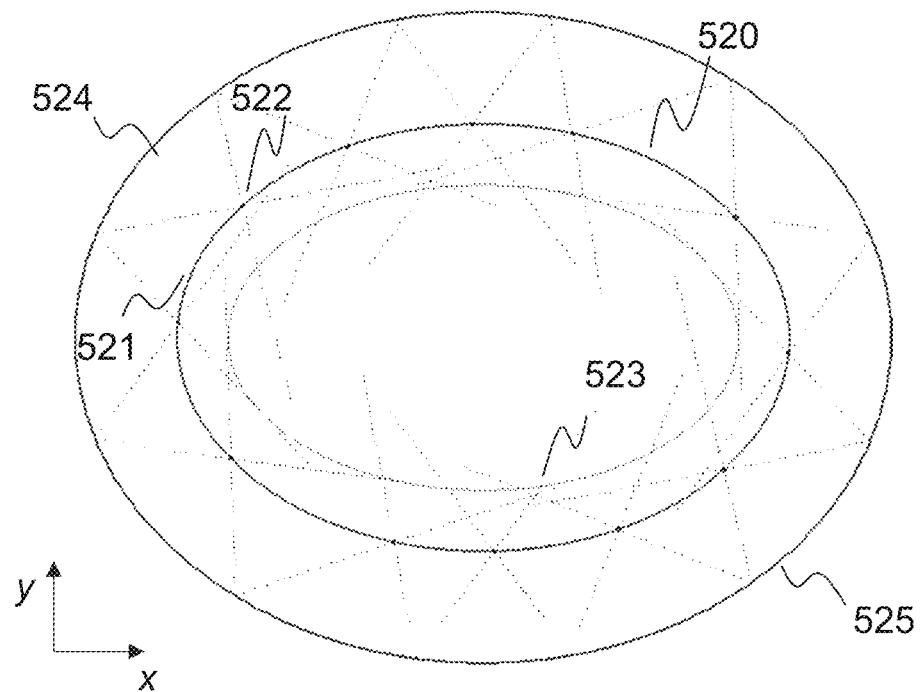

Referring to FIG. 5B, a cross section of the slit-plates of a collimator assembly in the whole-body scanning mode may be illustrated. In some embodiments, the collimator assembly 520 and the detector assembly 525 may be similar to or same as those in FIG. 5A.

In the whole-body scanning mode, the FOV 523 may be oval. And the FOV 523 may be centered on the axis of the detector assembly 525. In some embodiments, the size of the FOV 523 may be set to accommodate the whole body of an imaged subject. In some embodiments, the shape, location, and/or size, of the FOV 523 may be set by a user, according to a default setting of the imaging system 100, etc.

The slit-plates may be positioned at certain locations during the whole-body scanning mode. The location of a slit-plate may be determined based on one or more scanning parameters including, for example, FOV, spatial resolution, sensitivity, etc. In some embodiments, the locations of the slit-plates may be determined according to the FOV. The slit-plates may be positioned at certain locations to encompass the FOV 523. In some embodiments, the shape formed by the slit-plates may be oval. As illustrated in FIG. 5B, the four slit-plates may connect to each other with end to end, to form an oval encompassing the FOV 523.

The number of slits used in the whole-body scanning mode may be the same as or more than that in the head scanning mode. In some embodiments, the slit-plates or a part of it used in the whole-body scanning mode may be the same as those used in the head scanning mode.

Figure 5C:
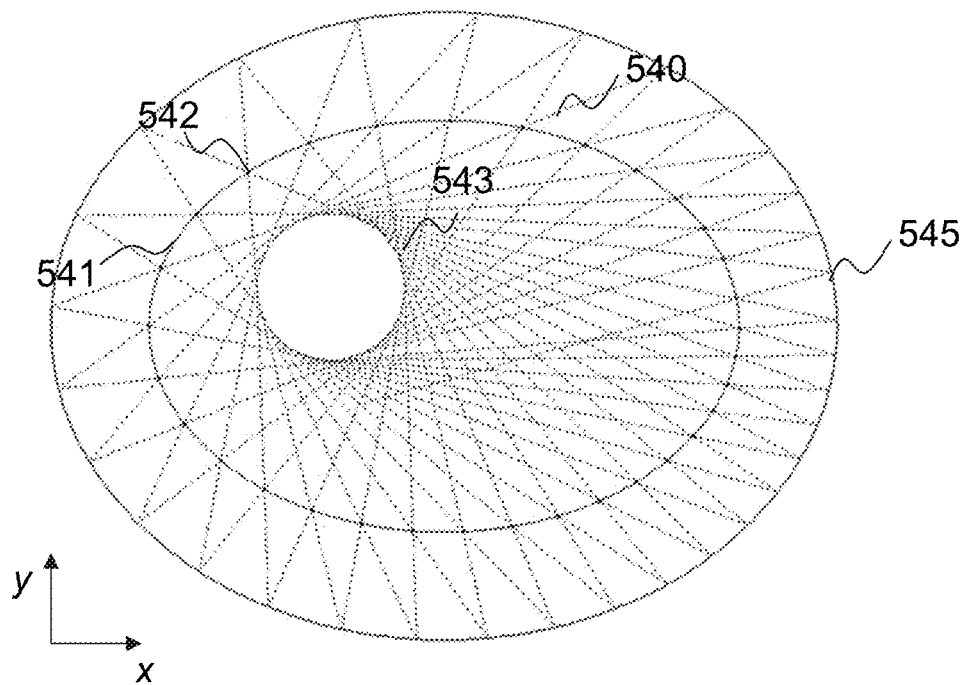

Referring to FIG. 5C, a cross section of the slit-plates of a collimator assembly in the heart scanning mode may be illustrated. In some embodiments, the detector assembly 545 and the slats of the collimator assembly 540 (not shown) may be similar to or same as the embodiments shown in FIG. 5A.

In the heart scanning mode, the FOV 543 may be circular for accommodating scanning of the heart of a patient. The position of the FOV 543 relative to the axis of the detector assembly 545 may be determined according to the off-center location of the heart of a patient. In some embodiments, the shape, location, and/or size, of the FOV 543 may be set by a user, according to a default setting of the imaging system 100, etc.

The slit-plates may be positioned at certain locations during the heart scanning mode. In some embodiments, the locations of the slit-plates of the collimator assembly 540 may be the same as the embodiments shown in FIG. 5B.

In some embodiments, the number of slits used in the heart scanning mode may depend on the FOV and sensitivity. The sensitivity may relate to the number of slits used in the scanning process. For example, a larger number of slits may correspond to a higher sensitivity. In some embodiments, the number of slits used in the heart scanning mode may be more than that used in the head scanning mode and the whole-body scanning mode.

Figure 5D:
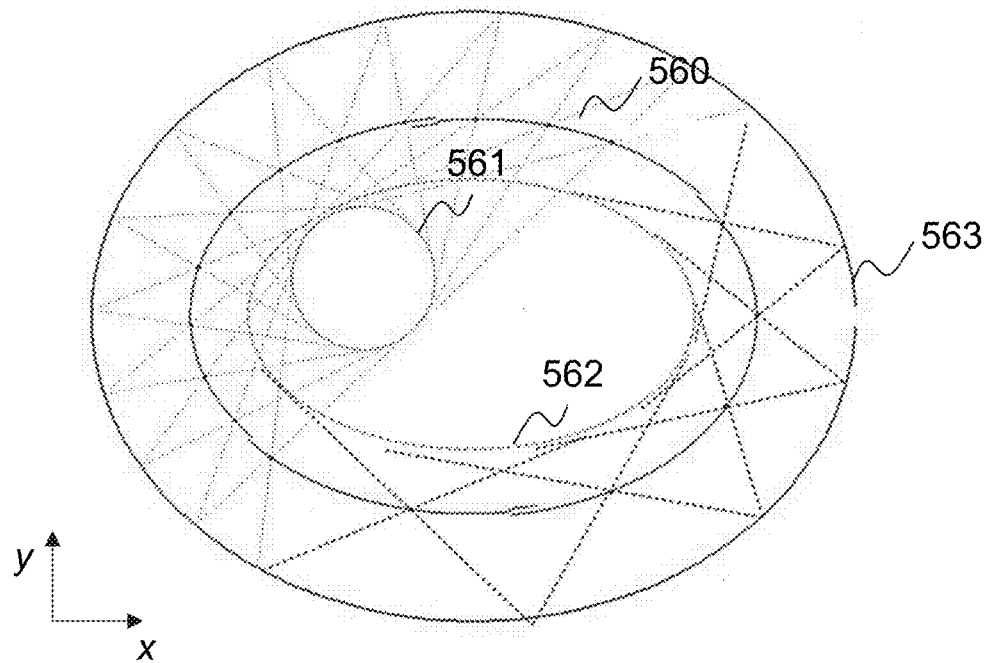

Referring to FIG. 5D, a cross section of the slit-plates of a collimator assembly in the heart scanning mode may be illustrated. In some embodiments, the embodiment described in FIG. 5D may be same as or similar to the descriptions with reference to FIG. 5C except than the detector assembly 563 may detect photons from two FOVs including a first FOV 561 and a second FOV 562. In some embodiments, the first FOV 561 may correspond to the heart of the patient. The second FOV 562 may correspond to the whole body of the patient.

The detector assembly 563 may include a plurality of detector units. The detector units may be positioned along the circumferential direction of the detector assembly 563 in x-y plane. In some embodiments, the photons from the first FOV 561 may be detected by a first set of detector units of the detector assembly 563, and the photons from the second FOV 562 may be detected by a second set of detector units of the detector assembly 563. In some embodiments, the detector units that is closer to the center of the FOV 561 (e.g., than a threshold distance set by a user) may be determined as the first set of detector units.

The detector assembly 563 may generate signals based on photons from the first FOV 561 and the second FOV 562. The signals may be transmitted to a computing device, for example, the computing device 140, to generate an image of the heart of a patient.

In some embodiments, the collimator assemblies and the detector assemblies illustrated in FIG. 5A through 5D may be implemented by a same scanner. In different scanning modes including head scanning mode, whole-body scanning mode, and heart scanning mode, the slit-plates of the collimator assembly may be placed in a plurality of locations. Thus the detector assembly may detect photons from different FOVs, and generate signals accordingly.

For example, with reference to FIG. 5A and FIG. 5B, the imaging system 100 may be in a head scanning mode and a whole-body scanning mode respectively. The imaging system 100 may switch between the head scanning mode and the whole-body scanning mode by switching the FOV between a first FOV corresponding to the head of a patient and a second FOV corresponding to the whole body of the patient. In some embodiments, the FOV may be switched between the first FOV and the second FOV by driving the four slit-plates in radial directions in the x-y plane to the locations shown in FIG. 5A and FIG. 5B.

As another example, with reference to FIG. 5B and FIG. 5C, the imaging system 100 may be in a whole-body scanning mode and a heart scanning mode respectively. The imaging system 100 may switch between the whole-body scanning mode and the heart scanning mode by switching the FOV between a second FOV corresponding to the whole body of a patient and a third FOV corresponding to the heart of the patient. In some embodiments, the FOV may be switched between the second FOV and the third FOV by driving the four slit-plates in the z-direction to place another part of the slits-plates, which may include a different number of slits, above the detector assembly. In some embodiments, the switch between different scanning modes may be implemented by a control device as described elsewhere in the present disclosure (e.g., FIG. 6 through FIG. 8, and the descriptions thereof).

Figure 6:
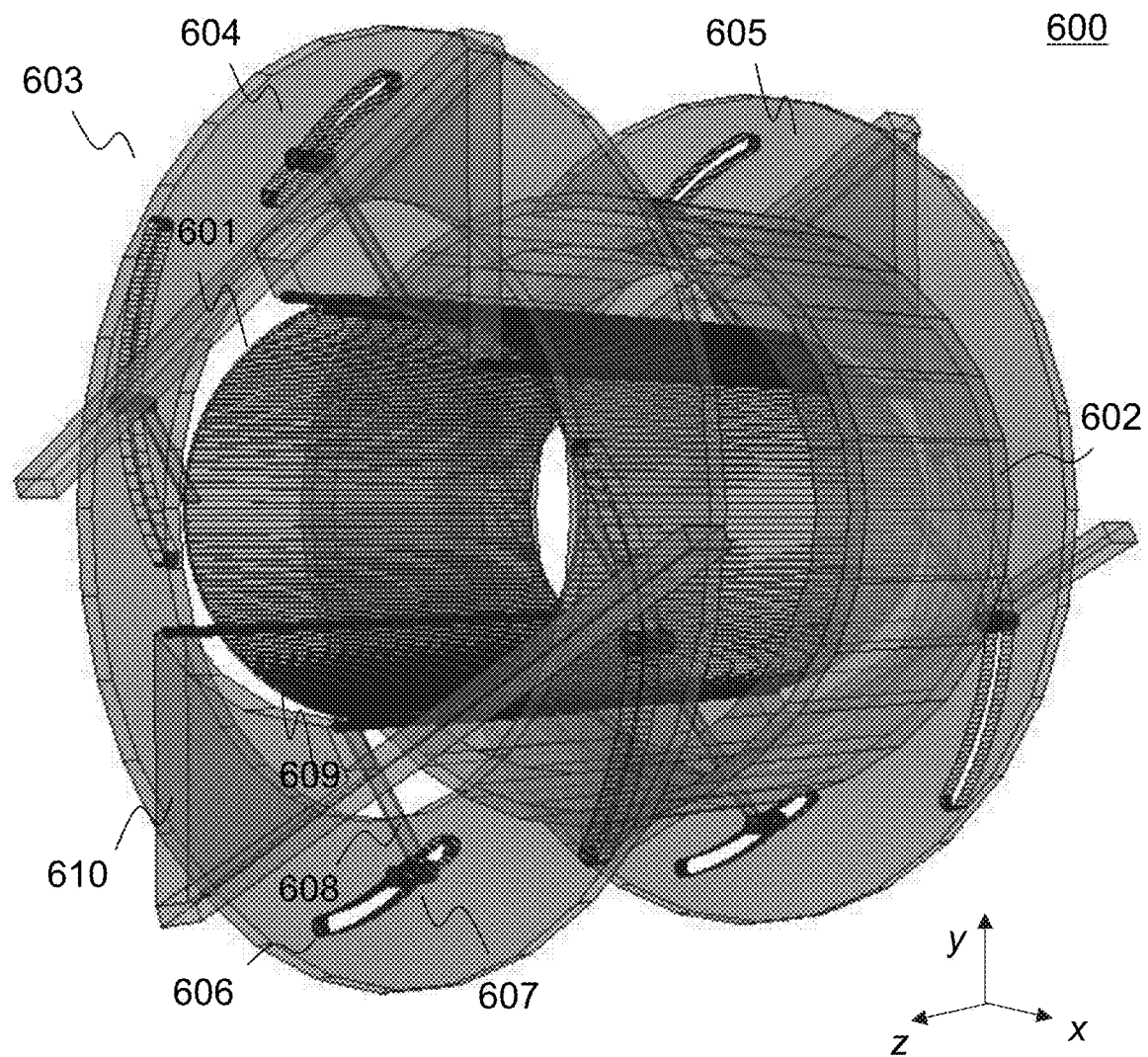
FIG. 6 is a perspective view of an exemplary scanner according to some embodiments of the present disclosure.

FIG. 6 is a perspective view of an exemplary scanner according to some embodiments of the present disclosure.

The scanner 600 may include a collimator assembly 601, a detector assembly 602, and a control device 603. The collimator assembly 601 may include a plurality of slit-plates and a plurality of slats (not shown). The plurality of slit-plates is configured as a flexible shape (e.g., a bore) surrounding an imaged subject. The slates may be positioned on a surface of the detector assembly 602. The detector assembly 602 may detect photons emitted from a FOV. In some embodiments, the detector assembly 602 may be stationary relative to the reference coordinate system 114. The cross section of the detector assembly 602 may be oval.

The control device 603 may be configured to drive the slit-plates to a plurality of locations. For example, the control device 603 may be configured to control at least one of the slit-plates to be moved from a first location to a second location to switch between different scanning modes and provide a plurality of fields of view. The plurality of fields of view includes a first field of view corresponding to a first scanning mode for scanning a first body part and a second field of view corresponding to a second scanning mode for scanning a second body part.

The control device 603 may include two shape-control devices 604 and 605.

The two shape-control devices 604 and 604 may be positioned in x-y planes (also referred to as a transverse planes of the imaging system 100). In some embodiment, each of the shape-control devices 604 and 605 may include an annular plate. The annular plates may have larger inner diameters than the diameter of the shape formed by the slit-plates of the collimator assembly 601 in x-y planes. The detector assembly 602 may be positioned between the two annular plates. In some embodiments, the length of the slit-plates in the z-direction may substantially equal to the distance between the two annular plates.

In some embodiments, each of the shape-control devices 604 and 605 may include a plurality of guide rails and a plurality of sliders. The plurality of guide rails may be fixed on the surface of the annular plates or embedded in the annular plates. In some embodiments, the guide rails may be grooves in the annular plates. The plurality of guide rails may be evenly distributed on the annular plates of the shape-control devices 604 and 605. For example, the guide rails may evenly distributed along the circumferential direction of the annular plates of the control devices 604 and 605. In some embodiments, the guide rails may have a plurality of shapes or sizes. For example, the guide rails may be an arc, a straight line, etc.

Each of the plurality of slider may slide in a guide rail. Merely for illustration purposes, the slider may be a ball, a block, a wheel, or the like, or a combination thereof. In some embodiments, each of the plurality of sliders may be connected to a slit-plate of the collimator assembly 601 through a connector, for example, a rod, a chain, a lever, or the like. As illustrated in FIG. 6, a slider 605 may slide in a guide rail 606. The guide rail 606 may be a groove on the annular plates of the shape-control device 604. The slider 607 may be connected to a slit-plate 609 through a rigid rod 608.

Thus the annular plates may connected to the at least one of the slit-plates, for example, through the guide rails, sliders, and/or a connector. The slit-plate 609 may be driven to a plurality of locations by moving of the annular plates of the shape-control devices 604 and 605. For example, when the annular plates of the shape-control devices 604 and 605 are driven to do axial rotation in x-y plane (e.g., from a first angle to a second angle), a stress may be applied to the slider 607 due to the moving of the guide rail 606 along with the annular plates of the shape-control device 604. The slider 607 may be driven to slide in the guide rail 606, and the slit-plate 609 may be moved to a predetermined location (e.g., the location as illustrated in FIG. 5A or FIG. 5B). As another example, when the shape-control devices 604 and 605 are driven to move in the z-direction, the collimator assembly 601 as well as the slit-plates may be moved to a plurality of locations. The detector assembly 602 may be stationary relative to the reference coordinate system 114. Thus the relative position of the slit-plates to the detector assembly 602 may be changed. For example, a certain part of the slit-plates with a larger number of slits may be positioned above the detector assembly 602.

In some embodiments, the control device 603 may further include a plurality of bore adjusting devices. The bore adjusting devices may facilitate the adjustment of the diameter of the bore of the scanner 600. The bore of a scanner may refer to the space within which a patient may be positioned. In some embodiments, the diameter of the bore may be referred to as the diameter of the opening space form by the slit-plates of the collimator assembly 601. The bore adjusting devices may be used to adjust of the diameter of the bore by driving the slit-plates to certain locations. For example, the bore adjusting devices may be used to increase the diameter of the bore by driving the slit-plates to farther locations relative to the center of the bore. The slit-plates may be driven, in radial directions in x-y plane (also referred to as a transverse plane of the imaging system 100), to farther locations. Merely for illustration purposes, a bore adjusting device 610 is described. The bore adjusting device 610 may be a rigid structure. The rigid structure may be connected to the slit-plates through one or more joints. In some embodiments, the slit-plates may be driven to a plurality of locations in radial directions relative to the center of the bore in x-y plane through the bore adjusting devices.

The control device 603 may also include a plurality of actuating devices (not shown) for actuating the shape-control devices and/or the bore adjusting devices. The actuating device may be any device that is capable of providing a force to drive the shape-control devices (e.g., to do axial rotation or to move to a certain location in the z-direction) and/or the bore adjusting devices (e.g., to move in radial direction in x-y plane). Merely by ways of example, the actuating device includes a hydraulic actuator, a pneumatic actuator, an electric actuator (e.g., an electrical motor), a thermal actuator, a magnetic actuator, a mechanical actuator, or the like, or a combination thereof.

Figure 7A:
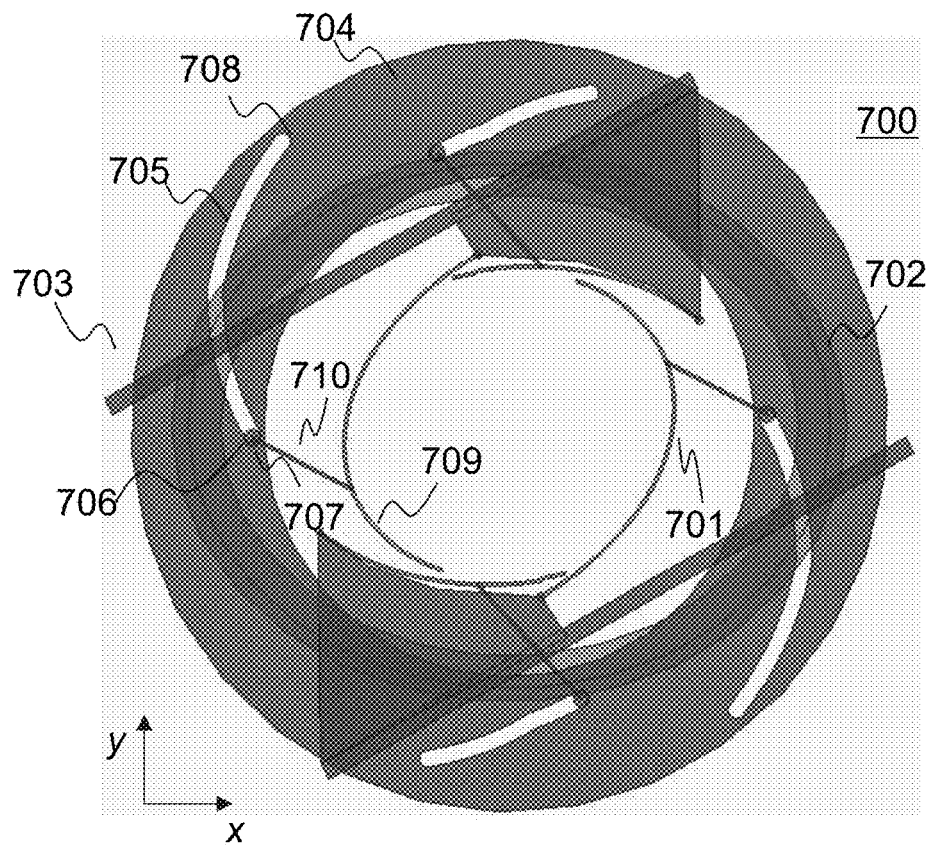
FIGS. 7A through 7C are schematic diagrams illustrating cross-sectional views of an exemplary scanner in different scanning modes according to some embodiments of the present disclosure.
Figure 7B:
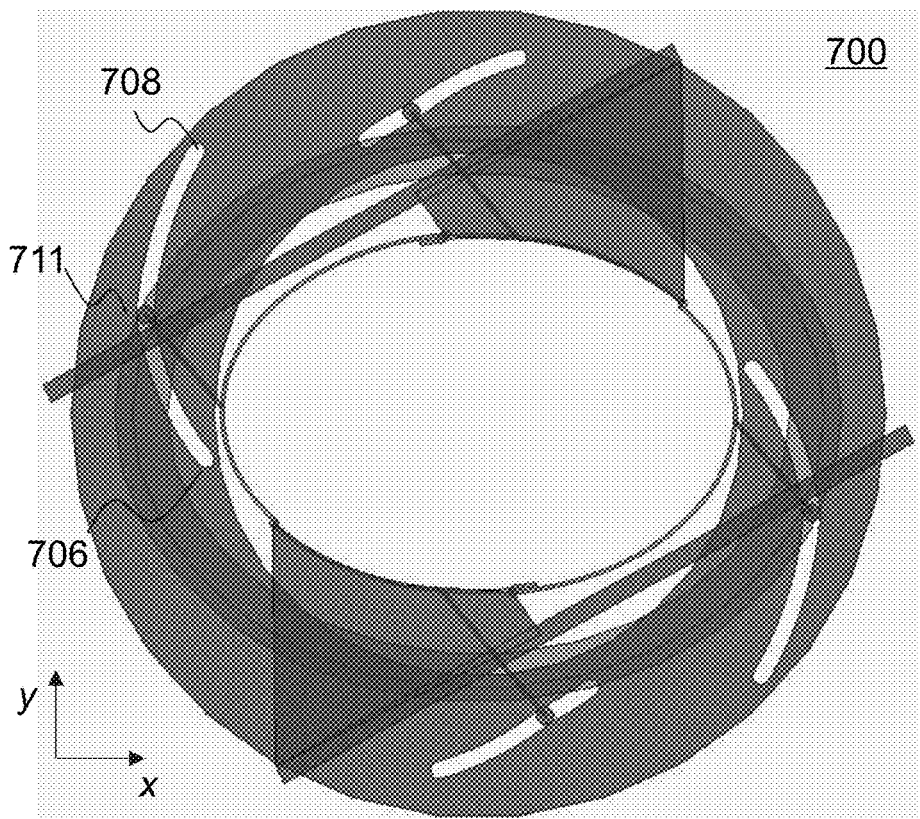
Figure 7C:
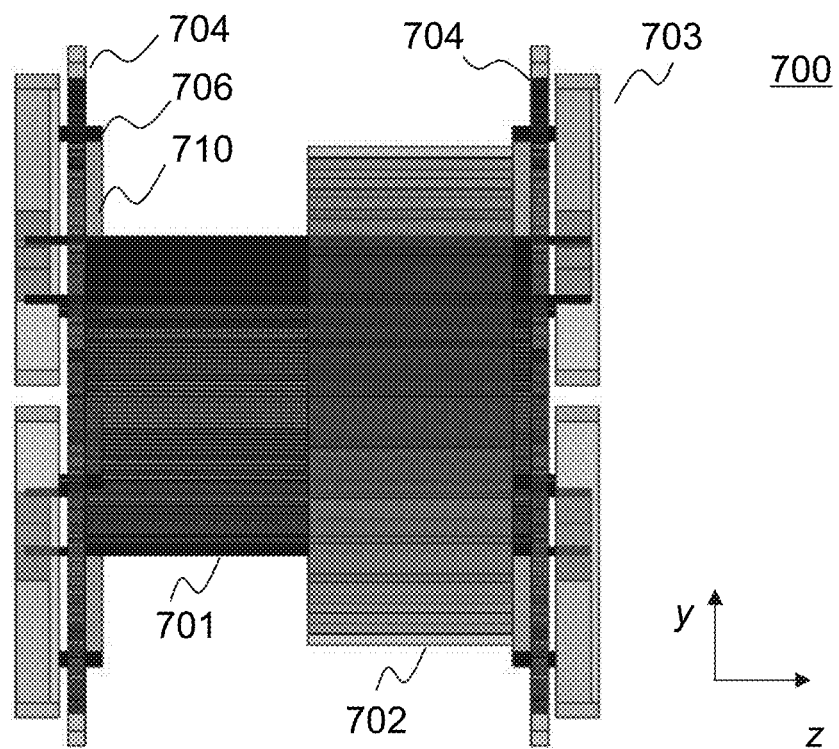

FIGS. 7A through 7C are schematic diagrams illustrating cross-sectional views of an exemplary scanner in different scanning modes according to some embodiments of the present disclosure. Referring to FIG. 0.7A, a cross section of the scanner 700 in the head scanning mode may be illustrated. The scanner 700 may include a collimator assembly 701, a detector assembly 702, and a control device 703. The collimator assembly 701 may include four slit-plates, which may form a flexible shape. In the head scanning mode, the FOV of the imaging system 100 may be circular and the four slit-plates of the collimator assembly 701 may be configured to form a circular shape as described with reference to FIG. 5A. The detector assembly 702, which is located behind the collimator assembly 701, may be stationary relative to the reference coordinate system 114. In some embodiments, the cross section of the detector assembly 702 may be oval.

The control device 703 may include a plurality of shape-control devices 704. The shape-control devices 704 may include annual plates on which a plurality of guide rails may be embedded. In some embodiments, the guide rails may be arc-shaped grooves evenly embedded in the annual plates of the shape-control devices 704 along its circumferential direction. Taking a guide rail 705 as an example, a slider 706 may slide in the guide rail 705. In some embodiments, the slider 706 may be located at the bottom 707 of the guide rail 705 in the head scanning mode. The slider 706 may be connected to a slit-plate 709 through a rigid plate 710.

The control device 703 may include an actuating device (not shown) such as an electrical motor. The actuating device may drive the annual plates of the shape-control devices 704 to do axial rotation in x-y plane. In some embodiments, the shape formed by the slit-plates of the collimator assembly 701 may be flexibly adjusted, and the scanner 700 may switch between the head scanning mode and the whole-body scanning mode by rotating the shape-control devices 704.

In some embodiments, the annual plates of the shape-control devices 704 may rotate in clockwise. A stress may be applied to the slider 706 because of the movement of the guide rail 705 along with the annual plates of the shape-control devices 704. The slider 706 may slide from the bottom 707 to the top 708 of the guide rail 705 upon the stress. The slit-plate 709, which is connected to the slider 706, may be driven to different locations in a radial direction of the annual plates of the shape-control devices 704. During this process, the FOV as well as the shape formed by the slit-plates may be changed (e.g., be enlarged).

When the slider 706 is moved to a certain location, for example, the location 711 as illustrated in FIG. 7B, the whole-body scanning mode may be initiated. The FOV may be oval in the whole-body scanning mode, and the slit-plates may form an oval shape as described with reference to FIG. 5B.

In some embodiments, the actuating device may drive the shape-control devices 704, as well as the slit-plates of the collimator assembly 701, to move in the z-direction. In some embodiments, the number of slits used in the scanning may be altered, and the scanner 700 may switch between the whole-body scanning mode and the heart scanning mode by moving the shape-control devices 704 in the z-direction.

In some embodiments, the slit-plates, which extends in the z-direction, may be longer than the detector assembly 702. For example, the length of the slit-plates may be twice the length of the detector assembly 702 in the z-direction. The slit-plate may include a plurality of segments in the z-direction. At least one of the plurality of segments may include a different number of slits. For example, a first segment of the slit-plates corresponding to a range of z=0-10 in the reference coordinate system 114 may include twenty slits, and a second segment of the slit-plates corresponding to another range of z=10~20 may include one hundred slits.

When the shape-control devices 704, as well as the slit-plates of the collimator assembly 701, is moved to a certain location, for example, as illustrated in FIG. 7C, the heart scanning mode may be initiated. At the certain location, a different segment with a different number of slits may be positioned above the detector assembly 702. The FOV may be changed accordingly as described with reference to FIG. 5C and/or FIG. 5D.

It should be noted that the above description of the scanner 700 is merely provided for the purposes of illustration, and not intended to limit the scope of the present disclosure. For persons having ordinary skills in the art, multiple variations and modifications may be made under the teachings of the present disclosure. For example, the shape-control devices may be omitted, and the slit-plates may be directly driven to the certain locations (e.g., the locations shown in FIG. 5A through 5D, and/or the locations shown in FIG. 7A through 7C) by a plurality of actuating devices. However, those variations and modifications do not depart from the scope of the present disclosure.

Figure 8:
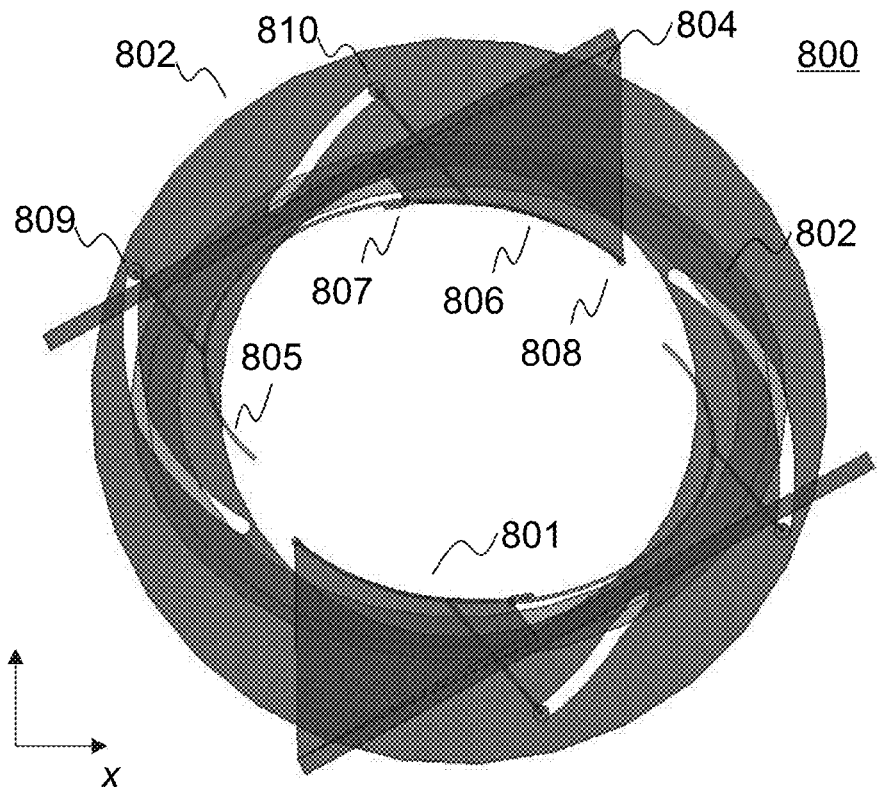
FIG. 8 is a schematic diagram illustrating a cross-sectional view of an exemplary scanner including a bore adjusting device according to some embodiments of the present disclosure.

FIG. 8 is a schematic diagram illustrating a cross-sectional view of an exemplary scanner including a bore adjusting device according to some embodiments of the present disclosure. Similar to the embodiments shown in FIG. 6, the scanner 800 may include a collimator assembly 801, a detector assembly 802, and a control device 803. The control device 803 may include a plurality of bore adjusting devices. The bore adjusting devices may be used to adjust the diameter of the bore of the scanner 800. In some embodiments, the diameter of the bore may be referred to as the diameter of the shape form by the slit-plates of the collimator assembly 801. Taking a bore adjusting device 804 as an example. The bore adjusting device 804 may be a plate includes a rigid rod and a junction plate. The junction plate may connect to the slit-plate 805 and 806 through joints 807 and 808 respectively.

The control device 803 may further include an actuating device. The actuating device may be coupled to the rigid rod to drive the rigid rod to move in the y-direction. In some embodiments, the rigid rod and the conjunction plate may be fixed together (e.g., by screws, adhesives, etc.). Thus, the slit-plates 805 and 806 may be driven, in radial directions in x-y plane, by the control device 803 to farther locations. In some embodiments, when the diameter of the bore is increased, the shape formed by the four slit-plates may be broken and the slit-plates may be separated from each other.

During the process of increasing the diameter of the bore of the scanner 800, the sliders 809 and 810, which respectively connect to the slit-plates 805 and 806 through rigid plates, may be passively moved toward the top of the guide rails. The bore may be at its largest diameter when the sliders reach the top of the corresponding guide rails.

It should be noted that the above description of the scanner 800 is merely provided for the purposes of illustration, and not intended to limit the scope of the present disclosure. For persons having ordinary skills in the art, multiple variations and modifications may be made under the teachings of the present disclosure. For example, the control device 803 may adjust the diameter of the bore by driving the bore adjusting device 804 to move in y-direction and driving the shape-control devices to do axial rotation in the meanwhile. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "module," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++,C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the descriptions, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. An imaging system, comprising:
    a collimator assembly configured to collimate photons emitted from an imaged subject, the collimator assembly comprising:
        a plurality of slit-plates, movable relative to each other and configured to form flexible shapes, each of the plurality slit-plates including one or more slits configured to collimate the photons in a first direction; and
        a plurality of slats parallel to a transverse plane of the imaging system;
    a detector assembly configured to generate signals based on the collimated photons; and
    a control device including two shape-control devices, each of the two shape-control devices including an annular plate, the detector assembly being positioned between the two annular plates, wherein the control device is configured to adjust the relative position between at least one of the plurality of slit-plates and the detector assembly to change a resolution of the imaging system by moving at least one of the two annular plates.

2. The system of claim 1, wherein the slit-plates are curved plates including multiple axially oriented slits, and wherein the one or more slits are perpendicular to the transverse plane of the imaging system.

3. The system of claim 1, wherein the plurality of slats are placed between the slit-plates and the detector assembly for collimating the photons in a second direction.

4. The system of claim 3, wherein the plurality of slats are evenly fixed on a surface of the detector assembly, and the detector assembly, as well as the plurality of slats, is stationary relative to a reference coordinate system.

5. The system of claim 1, wherein the plurality of slit-plates are movable in a radial direction in the transverse plane of the imaging system to form the flexible shapes.

6. The system of claim 5, wherein a side of at least one of the plurality of slit-plates is axially abutted with a surface of another slit-plate adjacent to the at least one of the plurality of slit-plates to form the flexible shapes.

7. The system of claim 5, wherein the flexible shapes include at least one of a circular shape or an oval shape.

8. The system of claim 1, wherein the plurality of slit-plates include at least two parts in an axial direction, wherein the at least two parts correspond to different number of slits.

9. The system of claim 8, wherein, to control at least one of the plurality of slit-plates to be moved from a first location to a second location, the control device is configured to control the plurality of slit-plates in the axial direction to place another part of the plurality of slit-plates above the detector assembly.

10. The system of claim 8, wherein, a length of the plurality of slit-plates is twice a length of the detector assembly in the axial direction.

11. The system of claim 1, wherein the detector assembly is an oval-shaped detector.

12. The system of claim 11, wherein the detector assembly include a first set of detector units and a second set of detector units, wherein the first set of detector units is configured to detect photons from a first field of view (FOV) corresponding a first body part of the imaged subject and the second set of detector units is configured to detect photons from a second FOV corresponding to a second body part of the imaged subject, wherein the first FOV and the second FOV correspond to different number of slits.

13. The system of claim 1, wherein a number of slits used in different scanning modes is altered.

14. An imaging system, comprising:
    a collimator assembly including:
        a plurality of slit-plates, movable relative to each other and configured to form flexible shapes, each of the plurality slit-plates including one or more slits; and a plurality of slats defining a number of channels between each two of the adjacent slats, the channels arranged nonparallel to the one or more slits;
a detector assembly placed outside of the collimator assembly; and
one or more control devices including two shape-control devices, each of the two shape-control devices including an annular plate, the detector assembly being positioned between the two annular plates, wherein the one or more control devices are configured to adjust the relative position between at least one of the plurality of slit-plates and the detector assembly to change a resolution of the imaging system by moving at least one of the two annular plates.

15. The system of claim 14, wherein the channels are substantially perpendicular to the slits.

16. The system of claim 14, wherein the two shape control devices are located at opposite ends of the detector assembly.

17. The system of claim 14, wherein the plurality of slit-plates are movable in a radial direction in the transverse plane of the imaging system to form the flexible shapes.

18. A method of adjusting collimator assembly performance, comprising:
moving at least one of a plurality of slit-plates of a collimator assembly to concurrently adjust a size of a field of view (FOV) surrounded by the collimator assembly;
wherein a detector assembly is placed outside of the collimator assembly, the plurality of slit-plates are movable relative to each other and configured to form flexible shapes, wherein the FOV corresponds to one of the flexible shapes, each of the plurality of slit-plates includes one or more slits, wherein the plurality of slats defines a number of channels between each two of the adjacent slats, and wherein the channels are arranged non-parallel to the one or more slits, wherein moving the at least one of the plurality of slit-plates of the collimator assembly includes:
moving at least one of two shape-control devices, wherein each of the two shape-control devices includes an annular plate, and the detector assembly is positioned between the two annular plates.

19. The method of claim 18, wherein the moving at least one of the plurality of slit-plates of the collimator assembly comprises controlling the at least one of the plurality of slit-plates to be moved in a radial direction in the transverse plane of the imaging system to form the flexible shapes.

20. The method of claim 18, wherein the moving at least one of the plurality of slit-plates of the collimator assembly comprises controlling the at least one of the plurality of slit-plates to be moved in the axial direction to place a part of the plurality of slit-plates above the detector assembly.

* * * * *